(12) United States Patent
Nawana et al.

(10) Patent No.: US 12,372,541 B2
(45) Date of Patent: Jul. 29, 2025

(54) POINT-OF-COLLECTION GRAPHENE-BASED TOXICOLOGY SENSOR

(71) Applicant: Graphene-DX, Inc., Boston, MA (US)

(72) Inventors: Namal Nawana, Weston, MA (US); Mehdi Abedi, Brighton, MA (US); Reza Mollaaghababa, Natick, MA (US)

(73) Assignee: GRAPHENE-DX, INC., Boston, MA (US)

( * ) Notice: Subject to any disclaimer, the term of this patent is extended or adjusted under 35 U.S.C. 154(b) by 449 days.

(21) Appl. No.: 17/152,513

(22) Filed: Jan. 19, 2021

(65) Prior Publication Data

US 2021/0223271 A1  Jul. 22, 2021

Related U.S. Application Data

(60) Provisional application No. 62/962,717, filed on Jan. 17, 2020.

(51) Int. Cl.
*G01N 33/94* (2006.01)
*A61B 5/00* (2006.01)
(Continued)

(52) U.S. Cl.
CPC ......... *G01N 33/946* (2013.01); *A61B 5/4845* (2013.01); *G01N 27/4145* (2013.01); *G01N 33/5438* (2013.01)

(58) Field of Classification Search
CPC ...... G01N 33/50; G01N 33/53; G01N 33/543; G01N 33/54366; G01N 33/54373;
(Continued)

(56) References Cited

U.S. PATENT DOCUMENTS

2015/0343144 A1   12/2015   Altschul et al.
2016/0283703 A1   9/2016    Allyn
(Continued)

FOREIGN PATENT DOCUMENTS

| CN | 103607960 A | 2/2014 |
| CN | 205643360 U | 10/2016 |
| WO | 2018200794 A1 | 11/2018 |

OTHER PUBLICATIONS

Karlsson et al., "Chemical Sensors Generated on Wafer-Scale Epitaxial Graphene for Application to Front-Line Drug Detection", Sensors 2019, 19, 2214, 14 pages (Year: 2019).*

(Continued)

*Primary Examiner* — Christopher L Chin
(74) *Attorney, Agent, or Firm* — Potomac Law Group, PLLC

(57) ABSTRACT

In one aspect, a sensor for detecting a drug of abuse (DOA) in a sample is disclosed. In some embodiments, the sensor includes a graphene layer, a plurality of binding agents, which bind to the DOA, coupled to said graphene layer to generate a functionalized graphene layer, and a plurality of electrical conductors electrically coupled to said functionalized graphene layer for measuring an electrical property of said functionalized graphene layer. While in some embodiments, such binding agents are monoclonal antibodies, in other embodiments they are polyclonal antibodies.

2 Claims, 15 Drawing Sheets

(51) Int. Cl.
*G01N 27/414* (2006.01)
*G01N 33/543* (2006.01)

(58) Field of Classification Search
CPC .. G01N 33/5438; G01N 33/94; G01N 33/946; G01N 27/403; G01N 27/414; G01N 27/4145; G01N 33/551; A61B 5/4845
USPC ...... 204/403.01, 403.2, 403.03, 403.15, 409, 204/412, 229.8; 422/82.01; 435/287.2; 436/524, 806, 815, 816, 901
See application file for complete search history.

(56) References Cited

U.S. PATENT DOCUMENTS

| | | | |
|---|---|---|---|
| 2017/0146529 A1* | 5/2017 | Nagrath | ........... G01N 33/57492 |
| 2019/0079068 A1 | 3/2019 | Taslim et al. | |
| 2019/0317081 A1 | 10/2019 | Taslim et al. | |
| 2020/0011860 A1 | 1/2020 | Nawana et al. | |
| 2021/0117636 A1* | 4/2021 | Lin | ................... H01L 29/66431 |

OTHER PUBLICATIONS

Oueslati et al., "Highly sensitive and specific on-site detection of serum cocaine by a low cost aptasensor", Biosensors and Bioelectronics 108 (2018) 103-108, 6 pages (Year: 2018).*
Shaw et al., "Applications of electrochemical sensors: Forensic drug analysis," Current Opinion in Electrochemistry, May 16, 2027, vol. 3(1), pp. 23-28.
Office Action for Korean Patent Application No. 10-2022-7028177 issued on May 24, 2024.
Mikael Karlsson et al., "Chemical Sensors Generated on Wafer-Scale Epitaxial Graphene for Application to Front-Line Drug Detection", Sensors, 2019, vol. 19, pp. 1-14.
Office Action (First) issued May 18, 2025 for Chinese Patent Application No. 202180021527.0.

* cited by examiner

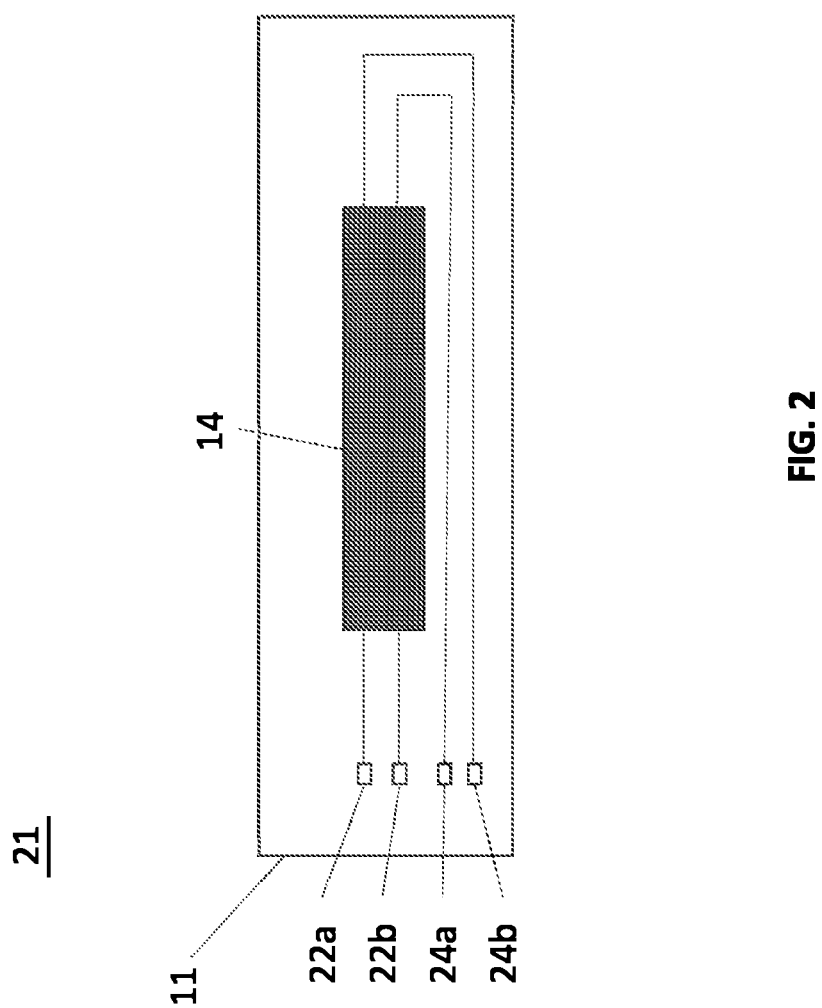

POINT-OF-COLLECTION GRAPHENE-BASED TOXICOLOGY SENSOR

CROSS-REFERENCE TO RELATED APPLICATIONS

This application claims priority to U.S. Provisional Application No. 62/962,717 filed on Jan. 17, 2020, which application is herein incorporated by reference in its entirety.

BACKGROUND

The present disclosure relates generally to a sensor and methods of using the sensor for testing a sample for the presence of a drug of abuse (DOA), such as cocaine, cocaine metabolites, amphetamines, and opiates therein.

A variety of devices for detecting drugs in different types of samples are known. For example, gas chromatography-mass spectrometry has been used for the detection of cocaine in human saliva. Further, point-of-collection testing (POCT) devices for the detection of drugs of abuse are also known, such as a mobile testing platform marketed by Abbott Laboratories under the trade designation DDS2™. Indeed, testing for such substances are performed using a wide variety of test samples (e.g., urine, saliva, blood) and a variety of testing methodologies as well as different types of facilities or locations.

The use of illicit or permitted drugs for medicinal and recreational use is subject to controls and benefits from monitoring to improve safety for the user and communities. The plethora of drugs in use make this monitoring task challenging due to workflow, accuracy, and cost.

There is a need for improved systems for rapid and accurate testing for drugs of abuse, such as cocaine, and particularly for such systems that can be employed as POCT devices, but also for less costly laboratory-based systems.

SUMMARY

In one aspect, a sensor for detecting a DOA (such as cocaine) in a sample is disclosed, which can be utilized to detect the DOA either via a single or multiple testing iterations performed on the sample. The sensor can include a graphene layer, a plurality of anti-DOA binding agents (e.g., antibodies and/or aptamers such as anti-cocaine antibodies and/or aptamers) that are coupled to said graphene layer, e.g., via π-π interactions, to generate a functionalized graphene layer, and a plurality of electrical conductors that are electrically coupled to said functionalized graphene layer (typically to a portion of the graphene layer to which the anti-DOA binding agents are not coupled) for measuring an electrical property of said functionalized graphene layer. The anti-DOA binding agents, e.g., antibodies and/or aptamers, can exhibit specific binding to each tested analyte. While in some embodiments, such binding agents are monoclonal antibodies, in other embodiments they can be polyclonal antibodies.

In some embodiments, the sensor can further include a reference electrode for applying a reference AC signal, e.g., an AC voltage, (herein also referred to as an "AC signal"), and in some embodiments as well as a DC offset voltage (e.g., a DC ramp voltage, which is herein also referred to as a "DC signal") to the functionalized graphene layer. By way of example, the reference AC signal can have a frequency in a range of about 1 kHz to about 1 MHz, such as in a range of about 10 kHz to about 100 kHz, or in a range of about 50 kHz to about 200 kHz, or in a range of about 200 kHz to about 300 kHz, or in a range of about 400 kHz to about 700 kHz, and the amplitude of the applied AC voltage (e.g., the peak-to-peak amplitude) can be, for example, in a range of about 100 millivolts to about 3 volts, e.g., in a range of about 1 volt to about 2 volts.

As noted above, in some embodiments, a DC ramp voltage is applied to the AC electrode, together with the AC voltage, during data acquisition. The DC ramp voltage can vary, for example, from about −10 volts to about 10 volts, e.g., in a range of about −5 volts to about +5 volts, or in a range of about −3 volts to about +3 volts, or in a range of about −1 volt to about +1 volt.

In a related aspect, a method of detecting a DOA in a sample is disclosed, which comprises applying the sample to a graphene layer functionalized with a plurality of anti-DOA binding agents (e.g., antibodies and/or aptamers), measuring at least one electrical property of the functionalized graphene layer, and using said measured electrical property to determine whether the DOA (e.g., cocaine) is present in said sample.

In some embodiments, the sample comprises a biological sample, such as a blood, urine or oral fluid. In some embodiments, the graphene layer is functionalized with aptamers and/or any other binding agent (e.g., an antibody fragment) that can exhibit specific binding with the DOA of interest.

In some embodiments, the electrical property of the functionalized graphene layer that is modulated in response to interaction of a DOA (e.g., cocaine) within a sample with the binding agent (e.g., an anti-cocaine antibody and/or aptamer) that is coupled to the graphene layer can be, for example, the electron mobility, and/or electrical impedance (e.g., a DC or an AC electrical resistance or both) of the functionalized graphene layer.

In a related aspect, a disposable cartridge for detecting a DOA (e.g., cocaine) in a sample is disclosed, which comprises a microfluidic component having an inlet port for receiving a sample and an exit port (herein also referred to as an outlet port), and a sensor that is fluidically coupled to said microfluidic component to receive at least a portion of said sample from said exit port, wherein said sensor comprises: a graphene layer, a plurality of anti-DOA binding agents (e.g., anti-DOA antibodies and/or aptamers) that are coupled to said graphene layer to generate a functionalized graphene layer, and a plurality of electrical conductors that are electrically coupled to said functionalized graphene layer (typically to portions of the graphene layer are that not functionalized with the anti-DOA binding agent) for measuring an electrical property (e.g., electron mobility, electrical impedance (e.g., DC and/or AC electrical resistance)) of said functionalized graphene layer.

In some embodiments, the microfluidic component can be formed of a polymeric material, such as PDMS or PMMA.

In some embodiments, the limit of detection of a sensor according to the present teachings is at least about 30 ng/mL, or at least about 40 ng/mL, or at least about 50 ng/ml, or at least about 100 ng/mL.

As discussed in more detail below, the present teachings can be employed for detecting a variety of drugs of abuse and their metabolites, e.g., metabolites of cocaine, amphetamine, and opiates (e.g., morphine).

Further understanding of various aspects of the present teachings can be obtained by reference to the following detailed description in conjunction with the associated drawings, which are described briefly below.

BRIEF DESCRIPTION OF THE DRAWINGS

The drawings are not necessarily to scale or exhaustive. Instead, emphasis is generally placed upon illustrating the principles of the embodiments described herein. The accompanying drawings, which are incorporated in this specification and constitute a part of it, illustrate several embodiments consistent with the disclosure. Together with the description, the drawings serve to explain the principles of the disclosure.

FIG. 2 is a schematic view of a graphene-based sensor according to an embodiment including a plurality of metallic pads for measuring an electrical property thereof in response to interaction with a sample under study.

DETAILED DESCRIPTION

Figure 1A:
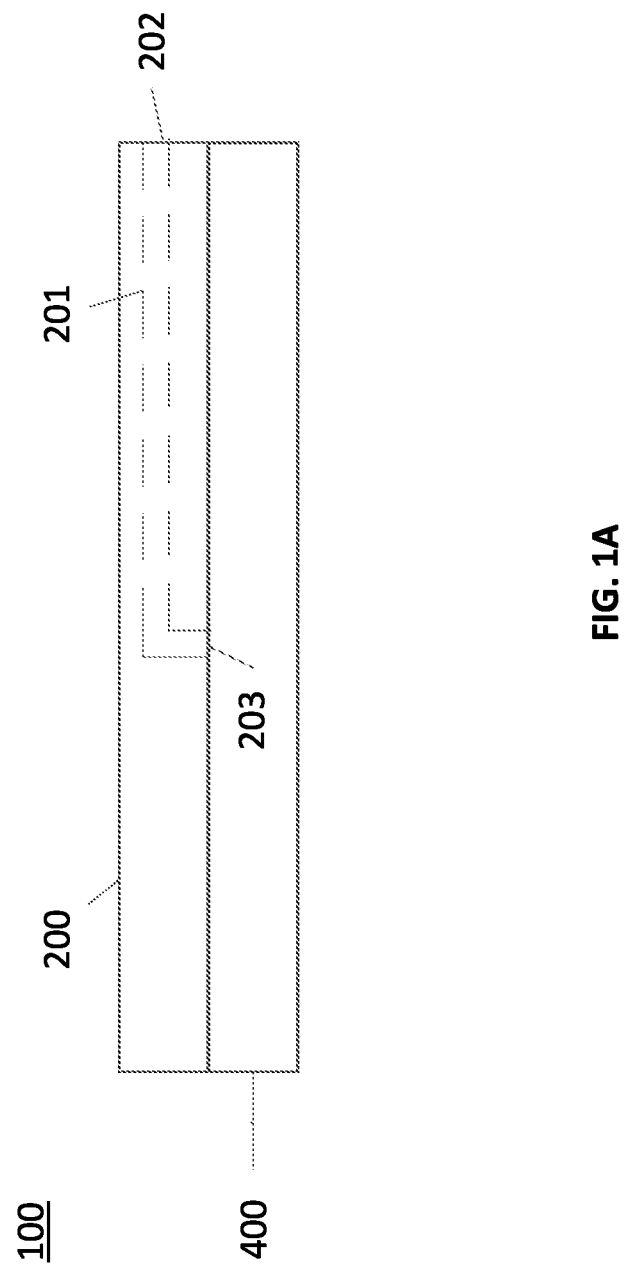
FIG. 1A schematically depicts a disposable cartridge according to an embodiment for detecting cocaine in a sample, FIG. 1B schematically depicts a graphene-based sensor employed in the cartridge depicted in FIG. 1A.

The present disclosure relates generally to a sensor, which can be implemented as a disposable cartridge in some embodiments, having a graphene-based sensing unit that can be employed for detecting a DOA and/or one or more of its metabolites (e.g., cocaine and/or its metabolites) in a sample, such as a biological sample. Although the following description is provided in connection with the detection of cocaine as an example of the DOA, the term "DOA" as used herein is not limited thereto. The term "DOA," as used herein, can refer to any compound or composition that can lead to social, physical, and emotional problems when used for purposes other than those for which they are meant to be used, or in excessive amounts. The DOA may be regulated or controlled. An example of such legislation is the Controlled Substances Act (CSA), and the U.S. Department of Justice Drugs Enforcement Administration (DEA) published a resource guide that lists various DOAs. The 2017 edition of "Drugs of Abuse—A DEA Resource Guide" is herein incorporated by reference in its entirety.

A DOA may be categorized as narcotics, stimulants, depressants, hallucinogens, marijuana/*cannabis*, steroids, inhalants, non-narcotic pain medicines, etc. Some examples of such DOAs that can be detected in a sample under investigation utilizing the present teachings can include, for example, alcohol (ethanol) (e.g., "drinking" alcohol), amphetamines/methamphetamines, antidepressants, barbiturates and hypnotics, benzodiazepines, cannabinoids, cocaine, flunitrazepam (Rohypnol), gamma hydroxybutyrate (GHB), opiates including codeine, oxycodone, and heroin, non-narcotic pain medicines including acetaminophen and anti-inflammatory drugs, phencyclidine (PCP), phenothiazines (antipsychotic or tranquilizing medicines), and prescription medicines of any type. However, the present teachings are not limited thereto, and the present teachings can be employed to identify various other compounds and/or compositions, which can also be classified as a DOA. As discussed below, the detection of such compounds can be achieved by utilizing a graphene layer that is functionalized with anti-DOA binding agents such that the coupling of the DOA, when present in a sample under investigation, with the anti-DOA binding agents can result in a change in at least one electrical property of the functionalized graphene layer, which can then be detected and analyzed to determine whether the DOA is present in the sample at a concentration above the sensor's limit-of-detection.

The term "DOA" as used herein may also include performance enhancing drugs (PED), which may be regulated in sports competitions.

The present disclosure provides teachings that allow the detection of any DOA in a sample under investigation via the binding of the DOA to a binding agent that is coupled to a graphene layer and measuring a change in at least one electrical property of the functionalized graphene layer. Some examples of such binding agents include, without limitation, an aptamer, an antibody, an antibody fragment, etc. In the following description, for ease of explanation, the term "antibody" is intended to refer to any suitable binding agent, i.e., any binding agent that exhibits specific binding to a DOA of interest.

The term "antibody," as used herein, may refer to a polypeptide that exhibit specific binding affinity, e.g., an immunoglobulin chain or fragment thereof, comprising at least one functional immunoglobulin variable domain sequence. An antibody encompasses full length antibodies and antibody fragments. In some embodiments, an antibody comprises an antigen binding or functional fragment of a full-length antibody, or a full-length immunoglobulin chain. For example, a full-length antibody is an immunoglobulin (Ig) molecule (e.g., an IgG antibody) that is naturally occurring or formed by normal immunoglobulin gene fragment recombinatorial processes. In embodiments, an antibody refers to an immunologically active, antigen-binding portion of an immunoglobulin molecule, such as an antibody fragment. An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody.

The term "antibody" also encompasses whole or antigen binding fragments of domain, or signal domain, antibodies, which can also be referred to as "sdAb" or "VHH." Domain antibodies comprise either VH or VL that can act as stand-alone, antibody fragments. Additionally, domain antibodies include heavy-chain-only antibodies (HCAbs). Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, hexavalent), or with higher orders of specificity (e.g., tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide.

The term "aptamer," as used herein, may refer to an oligonucleotide or a peptide molecule that exhibits specific binding to a target molecule. Aptamers are typically created by selecting them from a large random pool of oligonucleotide or peptide sequences, but natural aptamer do also exist.

The term "electrical property" as used herein may include electron mobility, electrical impedance (e.g., DC or AC electrical resistance or both), and electrical capacitance.

Various terms are used herein in accordance with their ordinary meanings in the art. For example, in some embodiments, the term "about" may denote a variation of at most 5%, %10, % 15, or % 20 around a numerical value. Further, the term "detection limit" as used herein may refer to a minimum concentration of an analyte, e.g., cocaine or cocaine metabolites, that can be positively detected using a sensor according to the present teachings.

FIG. 1A schematically depicts a cartridge 100 according to an embodiment. Cartridge 100 may be employed to detect cocaine in a sample, e.g., in a bodily fluid, such as urine, blood or oral fluid. In some embodiments, the cartridge 100 is a single-use and disposable cartridge.

The cartridge 100 includes a microfluidic delivery component 200 and a sensor 400. The microfluidic delivery component 200 may be configured to deliver a sample under investigation to the sensor 400.

In some embodiments, the microfluidic delivery component 200 may include at least one fluidic channel 201, an inlet port 202 for receiving a fluid (e.g., a liquid), and an outlet port 203 through which the fluid exits the microfluidic delivery component. The fluidic channel 201 may receive a sample at the inlet port 202 and deliver the sample to the sensor 400 at the outlet port 203. In some embodiments, the fluidic channel 201 may function based on capillary action. In some embodiments, the microfluidic delivery component 200 may be formed of a polymeric material, such as PDMS (polydimethylsiloxane) or PMMA (polymethyl methacrylate), and the fluidic channel may be formed via etching or other known techniques in the art.

Figure 1B:
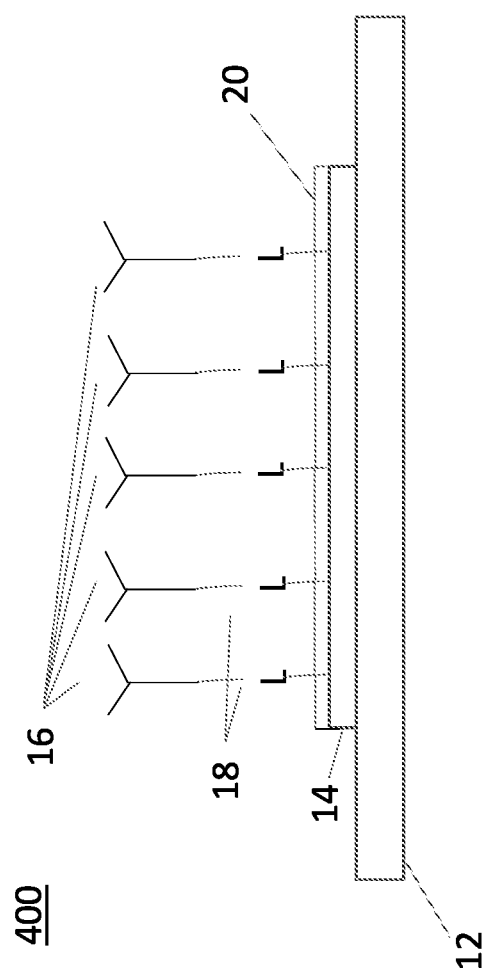

FIG. 1B depicts the sensor 400 according to some embodiments. The sensor 400 may include a graphene layer 14 and a substrate 12. As shown, in some embodiments, sensor 400 may be disposed on the underlying substrate 12. In various embodiments the substrate may be a semiconductor or a polymeric substrate. By way of example, in some embodiments, the substrate can be a silicon substrate while in other embodiments it can be a plastic substrate. For example, the underlying substrate can be formed of PDMS. Yet, in other embodiments, the underlying substrate can be a metallic substrate, such as a copper substrate.

In the embodiment shown in FIG. 1B, the graphene layer is functionalized with a plurality of binding agents (e.g., antibodies and/or aptamers) 16 that exhibit specific binding to a DOA such as cocaine (hereinafter also referred to as "antibodies 16"). Cocaine is a benzoid acid ester with a chemical formula of CnH21NO4 and the following chemical structure:

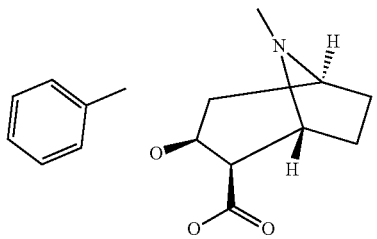

The antibodies 16 can be monoclonal or polyclonal antibodies, as discussed in more detail below. As shown schematically in FIG. 1B, a variety of linker molecules 18 can be employed for coupling the anti-cocaine antibodies to the underlying graphene layer. By way of example, in some embodiments, 1-pyrenebutonic acid succinimidyl ester is employed as a linker to facilitate the coupling of the anti-cocaine antibodies to the underlying graphene layer. In this embodiment, the plurality of anti-cocaine antibodies can cover a fraction of, or the entire, surface of the graphene layer. In various embodiments, the fraction can be at least about 60%, at least about 70%, at least about 80%, or 100% of the surface of the graphene layer. The remainder of the surface of the graphene layer (i.e., the surface areas not functionalized with the anti-DOA antibodies, other than, in some cases, the areas reserved for the coupling of electrical conductors to the graphene layer) can be passivated via a passivation layer 20. By way of example, the passivation layer can be formed using Tween 20, BLOTTO, BSA (Bovine Serum Albumin) and/or gelatin. The passivation layer can inhibit, and preferably prevent, the interaction of a sample of interest introduced onto the graphene layer with areas of the graphene layer that are not functionalized with the anti-cocaine antibodies. This can in turn lower the noise in the electrical signals that will be generated as a result of the interaction of the analyte of interest with the antibody molecules.

By way of example, in some embodiments, a graphene layer formed on an underlying substrate (e.g., a plastic, a semiconductor, such as silicon, or a metal substrate, such as a copper film) can be incubated with the linker molecule (e.g., a 5 mM solution of 1-pyrenebutonic acid succinimidyl ester) for a few hours (e.g., 2 hours) at room temperature.

The linker modified graphene layer can then be incubated with the antibody of interest in a buffer solution (e.g., NaCQ3-NaHCQ3 buffer solution (pH 9)) at a selected temperature and for a selected duration (e.g., 7-10 hours at 4 C), followed by rinsing with deionized (DI) water and phosphate buffered solution (PBS). In order to quench the unreacted succinimidyl ester groups, the modified graphene layer can be incubated with ethanolamine (e.g., 0.1 M solution at a pH of 9 for 1 hour).

Subsequently, the non-functionalized graphene areas can be passivated via a passivation layer, such as the passivation layer 20 schematically depicted in FIG. 1B. By way of example, the passivation of the non-functionalized portions of the graphene layer can be achieved, e.g., via incubation with 0.1% Tween 20.

A variety of commercially available anti-cocaine antibodies can be employed in the practice of the invention. By way of example, such an anti-cocaine antibody can be obtained from biorbyt of Cambridge, UK under the catalog number orb196380. In some embodiments, the anti-cocaine antibody can be the murine immunoglobulin G (IgG) cocaine-binding monoclonal antibody (mAb), GNC92H2, which is known its specificity for cocaine, as opposed to chemically-related cocaine metabolites, and for its moderately high affinity (K(d) approximately 200 nM) for cocaine. Further details regarding this antibody and its humanized form can be obtained by reference to an article entitled "Expression and characterization of a humanized cocaine-binding antibody," published in Biotechnology and Bioengineering 82 (5): 612-8, June 2003, which is herein incorporated by reference in its entirety.

FIG. 2 shows a sensor 21 according to some embodiments. The sensor 21 includes electrically conductive pads 22a, 22b, 24a and 24b, that allow four-point measurement of modulation of an electrical property of the functionalized graphene layer in response to interaction of cocaine present in a sample with the anti-cocaine antibodies coupled to the graphene layer. In particular, in this embodiment, the conductive pads 22a/22b are electrically coupled to one end of the functionalized graphene layer 14 and the conductive pads 24a/24b are electrically coupled to the opposed end of the functionalized graphene layer 14 to allow measuring a change in an electrical property of the underlying graphene layer caused by the interaction of cocaine in a sample under study with the anti-cocaine antibodies that are coupled to the graphene layer.

By way of example, in this embodiment, a change in at least one electrical property of the underlying graphene layer (e.g., electron mobility, electrical impedance, DC and/or AC electrical resistance, electrical capacitance, or the like) can be monitored to determine the presence of cocaine in a sample under study. By way of example, the DC resistance of the underlying graphene layer can be monitored to determine the presence of cocaine in a sample under study. In other embodiments, a change in electrical impedance of the graphene layer characterized, for example, by a combination of DC resistance and capacitance of the graphene/antibody system can be monitored to determine whether a target DOA is present in a sample under study. The electrically conductive pads can be formed using a variety of metals, such as copper and copper alloys, among others.

Figure 3A:
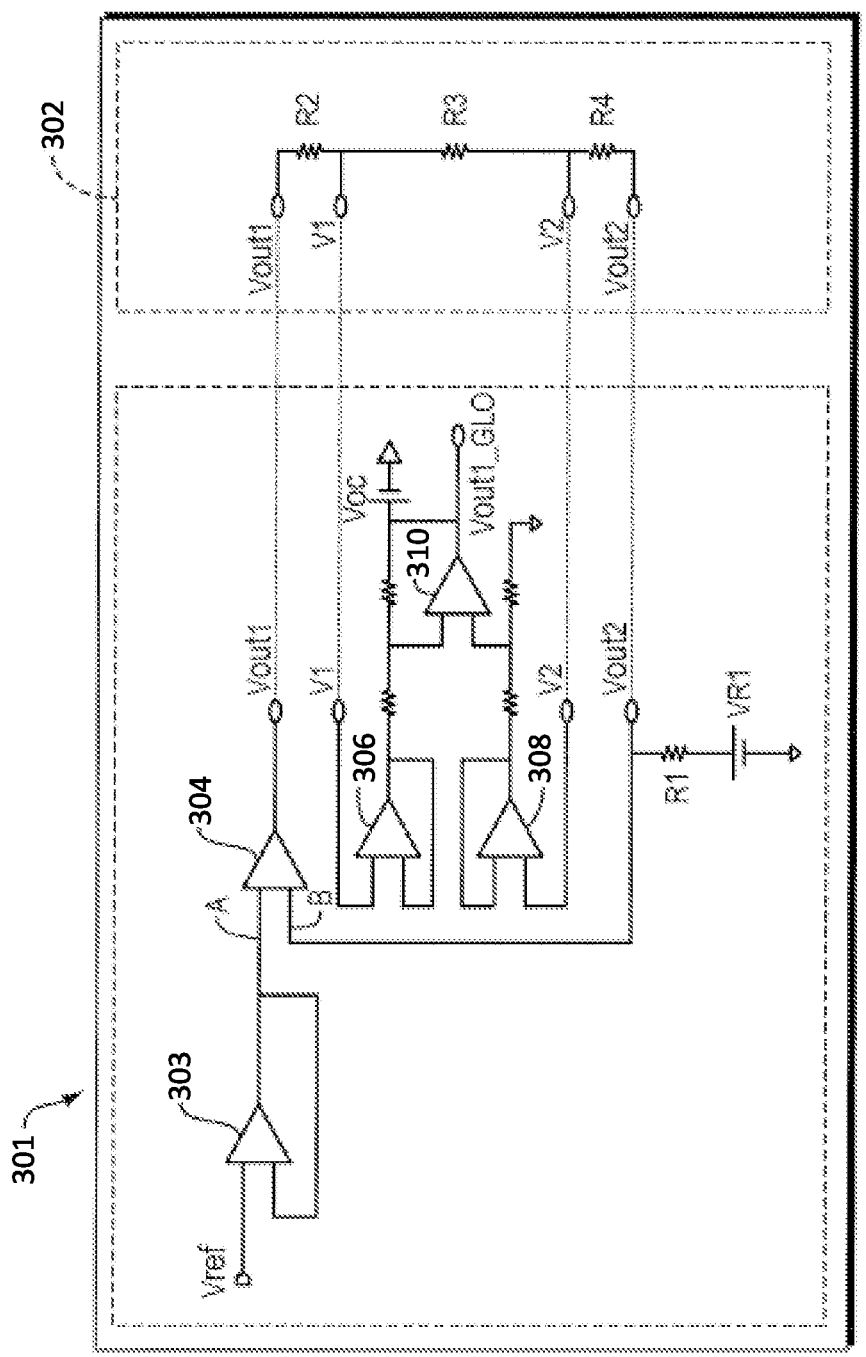
FIG. 3A depicts a circuit diagram of an example of a voltage-measuring device that can be employed for measuring a voltage induced across an antibody-functionalized graphene layer in response to application of a current thereto, FIG. 3B schematically depicts an analyzer in communication with the voltage-measuring device shown in FIG. 3A for receiving the voltage measured by the voltage-measuring device as well as the current applied to the antibody-functionalized graphene layer.

By way of example, FIG. 3A schematically depicts a voltage measuring circuitry 301 that can be employed in some embodiments of the present teachings. This figure shows a sensor 302 as an equivalent circuit corresponding to an antibody-functionalized graphene layer. A fixed voltage V (e.g., 1.2 V) is generated at the output of a buffer operational amplifier 303. This voltage is applied to one input (A) of a downstream operational amplifier 304 whose other input B is coupled to VR1 ground via a resistor R1. The output of the operational amplifier 304 (Vout1) is coupled to one end of the sensor 302 and the end of the resistor R1 that is not connected to VR1 ground is coupled to the other end of the sensor 302 (in this schematic diagram, resistor R2 denotes the resistance between two electrode pads at one end of the equivalent sensor 302, resistor R3 denotes the resistance of the graphene layer extending between two inner electrodes of the sensor, and resistor R4 denotes the resistance between two electrode pads at the other end of the sensor). As the operational amplifier maintains the voltage at the end of the resistor R1 that is not connected to VR1 ground at the fixed voltage applied to its input (A), e.g., 1.2 V, a constant current source is generated that provides a constant current flow through the sensor 702 and returns to ground via the resistor R1 and VR1.

The voltage generated across the antibody-functionalized graphene layer is measured via the two inner electrodes of the sensor. Specifically, one pair of the inner electrode pads is coupled to a buffer operational amplifier 306 and the other pair is coupled to the other buffer operational amplifier 308. The outputs of the buffer operational amplifiers are applied to the input ports of a differential amplifier 310 whose output port provides the voltage difference across the antibody-functionalized graphene layer. This voltage difference (Vout1–GLO) can then be used to measure the resistance exhibited by the antibody-functionalized graphene layer. The current forced through R3 is set by I=(Vref–VR1)/R1, where the value of VR1 is digitally controlled. For each value of current I, the corresponding voltage (Vout1_GLO) is measured and stored. The resistance of the antibody-functionalized graphene layer can be calculated as the derivative of the voltage, Vout1_GLO, with respect to current I, i.e., R=dV/di. In some embodiments, rather than a fixed known current, a fixed known voltage may be applied across the functionalized graphene layer and a change in the current, if any, in response to exposure of the functionalized graphene layer to a sample under investigation may be monitored for detecting a target DOA in the sample.

Figure 3B:
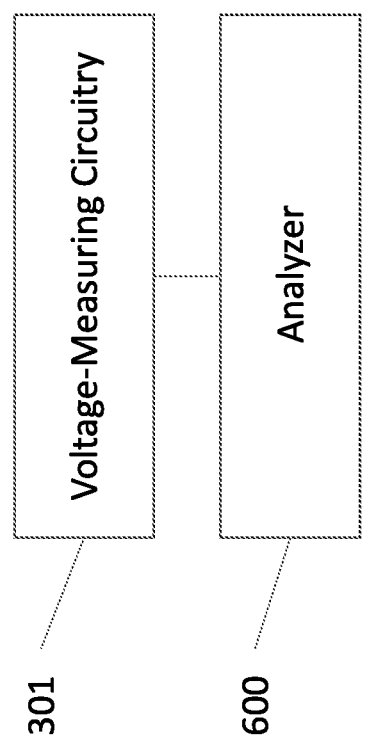
FIG. 3C depicts an example of implementation of the analyzer shown in FIG. 3A, FIG. 4A schematically depicts a sensor according to an embodiment, which includes an AC reference electrode, FIG. 4B schematically depicts a combination of a ramp voltage and an AC voltage applied to the reference electrode of a sensor according to an embodiment of the present teachings, FIG. 5 schematically depicts an array of graphene-based sensors in accordance with an embodiment, FIG. 6A schematically depicts a sensor according to an embodiment, which includes a plurality of sensing elements, FIG. 6B schematically depicts a microfluidic delivery component that can be incorporated in the sensor depicted in FIG. 6A, FIG. 7 schematically depicts a sensor having four sensing elements configured for detecting different drugs, FIG. 8 schematically depicts a sensor according to an embodiment, which includes a graphene-base sensing element in accordance with the present teachings and a fingerprint sensor for activating the sensor.

As shown schematically in FIG. 3B, in some embodiments, an analyzer 600 can be in communication with the voltage measuring circuitry 301 to receive the applied current and the measured voltage value and use these values to calculate the resistance of the antibody-functionalized graphene layer. The analyzer 600 can then employ the calculated resistance, e.g., a change in the resistance in response to exposure of the antibody-functionalized graphene layer to a sample under investigation, to determine, in accordance with the present teachings, whether the sample contains a DOA of interest, such as those listed herein.

Figure 3C:
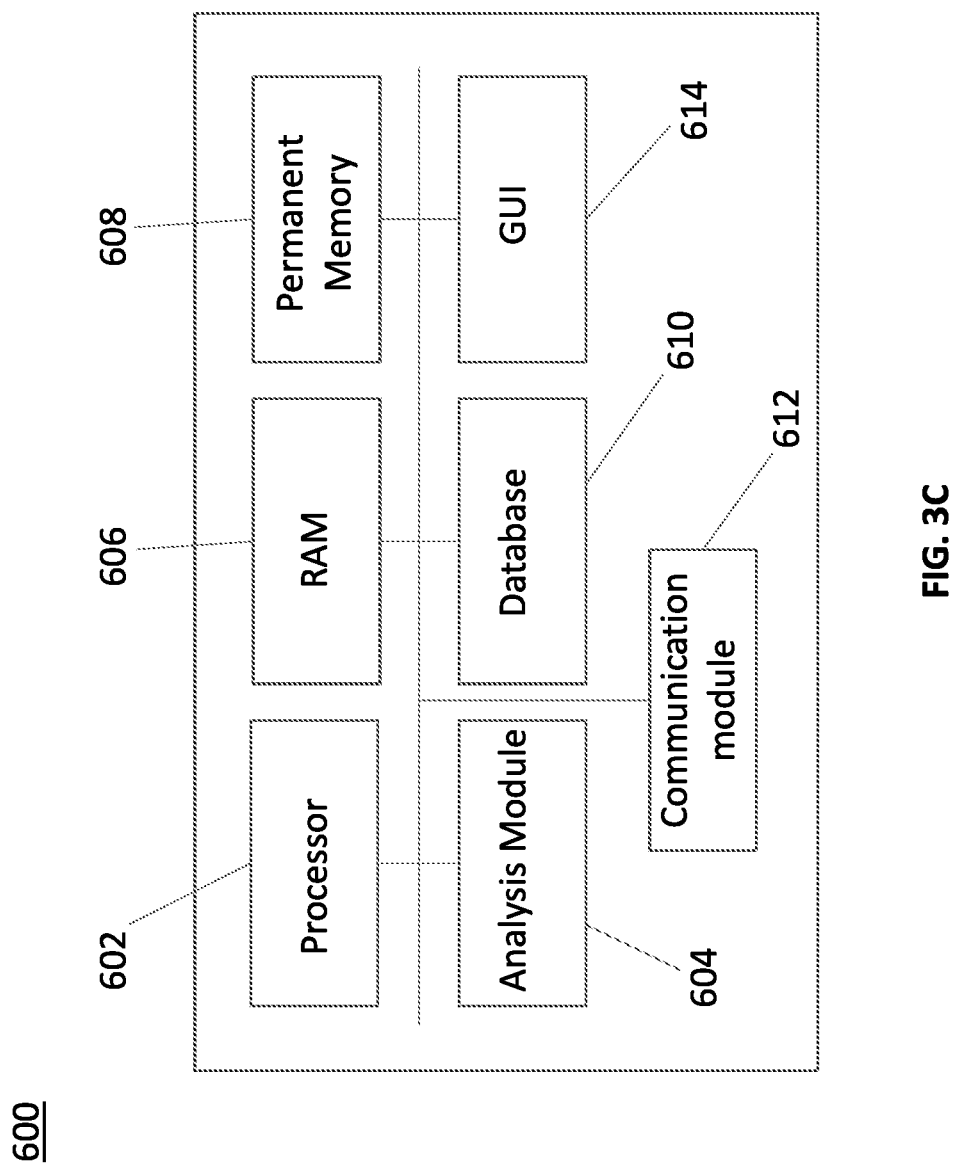

By way of example, as shown schematically in FIG. 3C, in this embodiment, the analyzer 600 can include a processor 602, an analysis module 604, a random-access memory (RAM) 606, a permanent memory 608, a database 610, a communication module 612, and a graphical user interface (GUI) 614. The analyzer 600 can employ the communication module 612 to communicate with the voltage measuring circuitry 301 to receive the values of the applied current and the measured voltage. The communication module 612 can be a wired or a wireless communication module. The analyzer 600 further includes a graphical user interface (GUI) 614 that allows a user to interact with the analyzer 600.

The analysis module 604 can employ the values of a current applied to the antibody-functionalized graphene layer as well as the voltage induced across the graphene layer to calculate a change in the resistance of the antibody-functionalized graphene layer in response to exposure thereof to a sample under investigation. The instructions for such calculation can be stored in the permanent memory 608 and can be transferred at runtime to RAM 606 via processor 602 for use by the analysis module 604. The GUI 614 can allow a user to interact with the analyzer 600.

In some embodiments, the analyzer 600 can include an AC (alternating current) source of current, which can apply an AC current having a known amplitude and frequency to the graphene layer. In particular, various embodiments can advantageously use an AC voltage having a frequency in a range of about 1 kHz to about 1 MHZ, e.g., in a range of about 10 kHz to about 500 kHz, or in a range of about 20 kHz to about 400 kHz, or in a range of about 30 kHz to about 300 kHz, or in a range of about 40 kHz to about 200 kHz. By way of example, the amplitude of the AC voltage applied to the graphene layer can be in a range of about 1 millivolt to about 3 volts, e.g., in a range of about 100 millivolts to about 2 volts, or in range of about 200 millivolts to about 1 volt, or in range of about 300 millivolts to about 1 volt, e.g., in a range of about 0.5 volts to 1 volt. Further, in some cases, the voltage applied to the reference electrode can have an AC component and a DC offset, where the DC offset can be in a range of about −40 volts to about +40 volts, e.g., −1 volt to about +1 volt.

The analyzer 600 can further include an ac voltmeter circuitry for measuring the ac voltage induced across the graphene layer in response to the application of the ac current to the layer. By measuring the amplitude and/or phase shift of the induced ac voltage, the electrical impedance of the graphene layer can be determined in a manner known in the art. In some embodiments in which an AC signal (e.g., an AC voltage or current) is applied to the graphene layer, a lock-in detection technique may be employed for the measurement of the response of the functionalized graphene layer to the applied AC signal. For example, in some such embodiments, a portion of the applied AC signal may used as the reference signal that is applied to a lock-in amplifier and an output signal of the functionalized graphene layer may be used as the input signal of the lock-in amplifier. The output signal of the lock-in amplifier can then provide the response of the functionalized graphene layer to its exposure to the sample under investigation.

Further details regarding a suitable analyzer that can be employed in the practice of some embodiments of the present teachings can be found, e.g., in U.S. Pat. No. 9,664,674 titled "Device and Method for Chemical Analysis," which is herein incorporated by reference in its entirety.

Figure 4A:
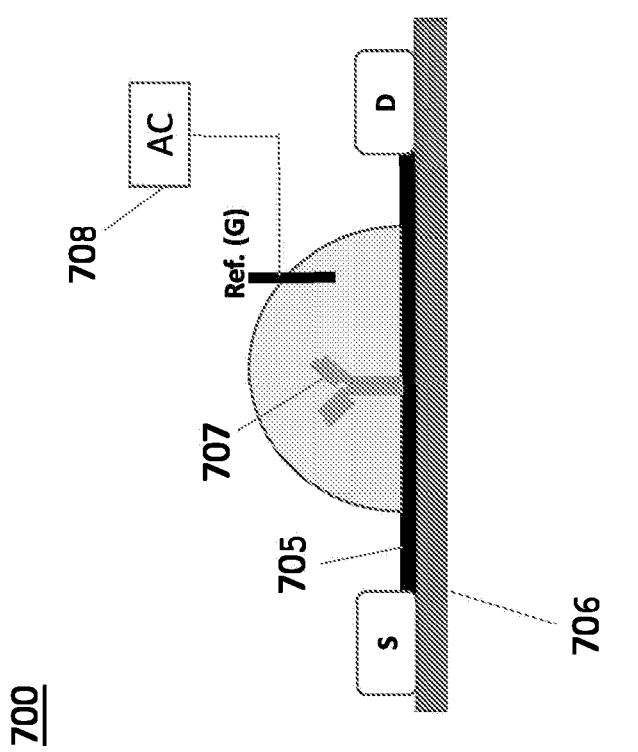

FIG. 4A schematically depicts another embodiment of a sensor 700 according to the present teachings. Sensor 700 includes a graphene layer 705 that is disposed on an underlying substrate 706, e.g., a semiconductor substrate, and is functionalized with a binding agent of interest 707, which can exhibit specific binding to a DOA (e.g., cocaine). A source electrode(S) and a drain electrode (D) are electrically coupled to the graphene layer to allow measuring a change in one or more electrical parameters of the functionalized graphene layer in response to interaction of the functionalized graphene layer with a sample. The sensor 700 further includes a reference electrode (G) that is disposed in proximity of the graphene layer.

In use, in some embodiments, a change in the electrical resistance of the functionalized graphene layer can be measured in response to the interaction of the functionalized graphene layer with a sample to determine whether a DOA (e.g., cocaine) is present in the sample. For example, when the sample contains cocaine above a certain concentration threshold (e.g., above the detection limit of a sensor), the interaction of the cocaine with the antibodies coupled to the graphene layer can cause modulation of an electrical property of the graphene layer (e.g., DC resistance) and hence provide a signal indicative of the presence of cocaine in the sample.

In some embodiments, the application of an AC (alternating current) voltage via an AC voltage source 708 to the reference electrode can facilitate the detection of one or more electrical properties of the functionalized graphene layer, e.g., a change in its resistance in response to the interaction of the antibody with an analyte exhibiting specific binding to the antibody. In particular, in some embodiments, the application of an AC voltage having a frequency in a range of about 1 kHz to 1 MHZ, e.g., in a range of about 10 kHz to about 500 kHz or in a range of about 20 kHz to about 100 kHz, can be especially advantageous in this regard. By way of example, the amplitude of the AC voltage applied to the reference electrode can be in a range of about 1 millivolt to about 3 volts, e.g., 0.5 volts to 1 volt. Further, in some cases, the voltage applied to the reference electrode can have an AC component and a DC offset, where the DC offset can be in a range of about −40 volts to about +40 volts, e.g., −1 volt to about +1 volt. In some embodiments, the DC offset can be applied to the reference electrode as a ramp voltage.

Figure 4B:
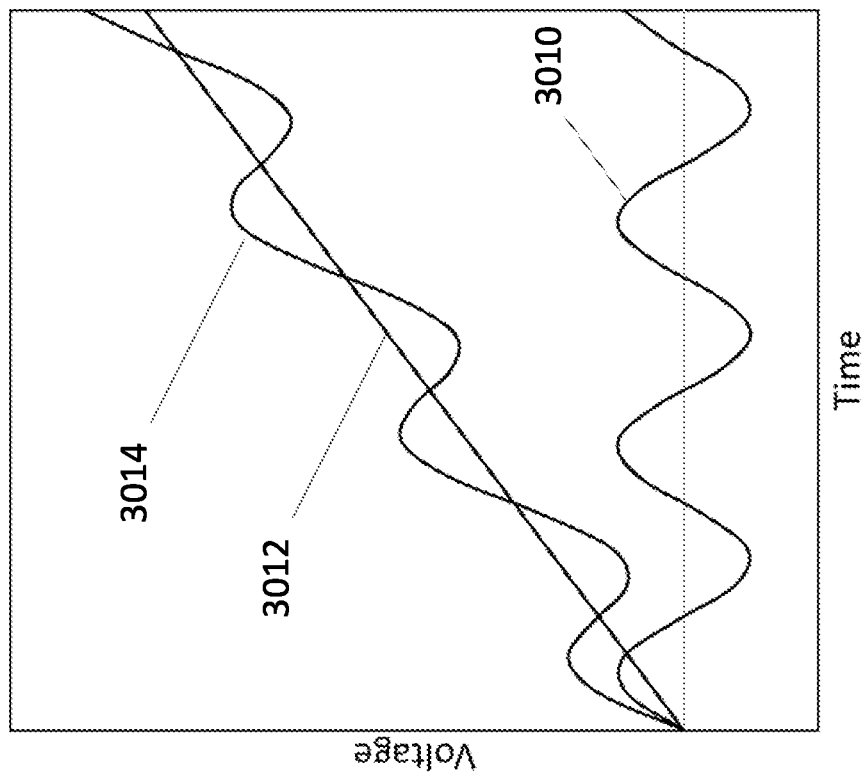

By way of illustration, FIG. 4B schematically depicts a combination of an AC voltage 3010 and a DC offset voltage 3012 applied to the reference electrode, resulting in voltage 3014. By way of example, the DC offset voltage can extend from about −10 V to about +10 V (e.g., from −1 V to about 1 V), and the applied AC voltage can have the frequencies and amplitudes disclosed above.

Without being limited to any particular theory, in some embodiments, it is expected that the application of a voltage such as voltage 3014 to the reference electrode can minimize, and preferably eliminate, an effective capacitance associated with a sample, e.g., a liquid sample, with which the functionalized graphene layer is brought into contact as the sample is being tested, thereby facilitating the detection of a change in the resistance of the underlying graphene layer in response to the interaction of the antibodies 703 with a respective antigen (i.e., DOA). In some cases, the effective capacitance of the sample can be due to ions present in the sample.

The sensors and the methods of the present teachings can be employed to detect the presence of a DOA in a variety of samples. For example, in some embodiments, such samples comprise biological samples, such as urine, blood or oral fluid. In some embodiments, the detection of the DOA is indicated when the DOA is present in a sample above a threshold that allows positive identification thereof based on the sensitivity of the sensor.

Figure 5:
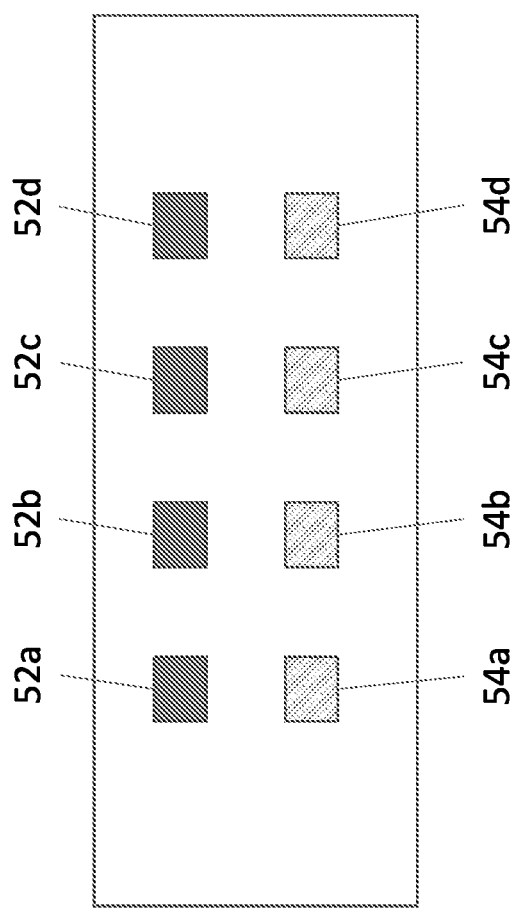

In some embodiments, a sensor according to the present teachings can include an array of sensing elements whose signals can be averaged to generate a resultant signal indicative of presence or absence of a DOA (e.g., above a predefined threshold) in a sample. By way of example, FIG. 5 schematically depicts such a sensor 50 having a plurality of sensing elements 52a, 52b, 52c, and 52d (herein collectively referred to as sensing elements 52), and sensing elements 54a, 54b, 54c, and 54d (herein collectively referred to as sensing elements 54).

Each of the sensing elements 52 and 54 can include a graphene layer functionalized with an anti-cocaine antibody and can have a structure similar to that discussed above in connection with sensor 50. In some embodiments, the different sensing elements can be functionalized with different types of antibodies (e.g., anti-cocaine antibodies). In some embodiments, the signals generated by the sensing elements 52 can be averaged to generate a resultant signal. Further, in some embodiments, at least one of the sensing elements 52 can be configured as a calibration sensing element to allow quantification of cocaine (or other target DOAs) present in a sample.

In some embodiments, the sensor 50 can be configured to detect one or more metabolites of cocaine, in addition or instead of cocaine. It is known that cocaine is metabolized by liver into two major, inactive metabolites, namely, benzoylecgonine (BE) and ecgonine methyl ester (EME). In some embodiments, the sensor 50 is configured to detect such metabolites of cocaine in a biological fluid, e.g., in the oral fluid. Oral fluid testing can be very effective monitoring tool for driving under the influence of drugs, drug treatment and parolee programs. By way of another example, heroin (diamorphine) is metabolized to 6-MAM morphine, codeine is metabolized to morphine, and oxycodone is metabolized to oxymorphone and noroxymorphone. The sensor 50 can be configured to detect these metabolites, among others.

More specifically, with reference to FIG. 1B, in some such embodiments, the antibodies 16 can be selected to bind specifically to either one of the above cocaine metabolites. For example, in some such embodiments, the antibodies 16 can exhibit specific binding to BE and in some other embodiments, the antibodies 16 can exhibit specific binding to EME. Antibodies that exhibit specific binding to BE or EME are commercially available. By way of example, some embodiments can employ a mouse BE monoclonal antibody marketed by MyBioSource, Inc. of San Diego, CA under the catalogue number MBS5692520. Some other embodiments can employ a commercially available EME antibody.

In some embodiments, the graphene layer may be functionalized with aptamers to bind specifically to a DOA, such as cocaine metabolites, BE, and EME. Aptamers that exhibit specific binding to cocaine metabolites, BE, or EME are commercially available. For example, the articles by Adegoke et al. published in Microchimica Acta, 187 (2), 2020, and by Kawano et al. published in J. Am. Chem. Soc. 133 (22), June 2011, which are herein incorporated by reference in their entirety, describe DNA aptamers that bind to the cocaine molecule. By way of example, in some embodiments, a DNA aptamer MNS-4.1 can be used.

The BE and/or EME antibodies can be coupled to the underlying graphene layer using the mechanisms discussed herein, including the use of 1-pyrenebutonic acid succinimidyl ester.

In some embodiments, a biological sample, e.g., oral fluid, can be brought into contact with the graphene layer functionalized with BE and/or EME antibodies. The interaction of such cocaine metabolites, when present in the sample above the detection limit of the sensor, can cause a change in at least one electrical property of the graphene layer, which can be measured, e.g., in a manner discussed above, to indicate the presence of the above cocaine metabolites in the sample.

In some embodiments, the detection limit of a sensor according to the present teachings for detecting any of cocaine or its metabolites, or more generally for the detection of any DOA can be, for example, 30 ng/mL, or at least about 40 ng/mL, or at least about 50 ng/mL, or at least about 100 ng/mL.

In some embodiments, a sensor according to the present teachings can include a plurality of sensing elements, where one or more of the sensing elements can be configured for detecting cocaine in a sample and one or more of the other sensing elements can be configured for detecting a cocaine metabolite in the sample.

Figure 6A:
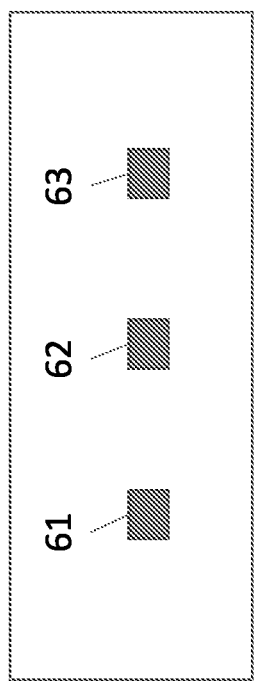

By way of example, FIG. 6A schematically depicts such a sensor 60, which includes three sensing elements 61, 62, and 63. In this embodiment, the sensing element 61 can include a graphene layer functionalized with an antibody that exhibits specific binding to a DOA (e.g., cocaine) while the sensing elements 62 and 63 can be functionalized, respectively, with an antibody that exhibits specific binding to one or more metabolites of the DOA, e.g., BE and EME.

Figure 6B:
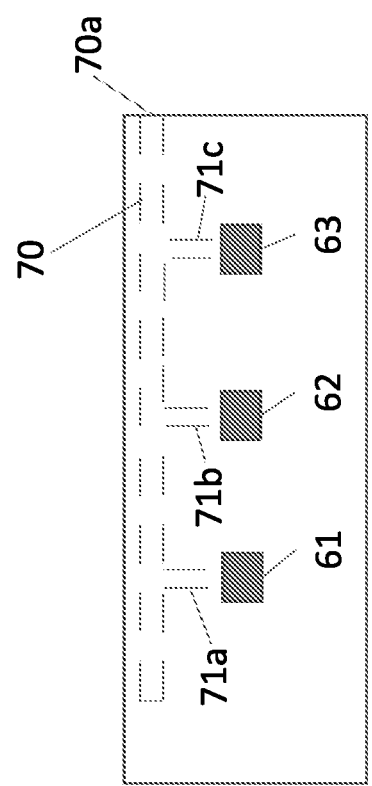

As shown schematically in FIG. 6B, a microfluidic delivery component can be coupled to the sensor 60 to deliver portions of a sample to the sensing elements 61, 62, and 63. In this embodiment, the microfluidic delivery component includes a microfluidic channel 70 having an inlet port 70a for receiving a sample. The microfluid channel 70 extends to three branches 71a, 71b, and 71c, each of which is configured to deliver a portion of a received sample to one of the sensing elements 61, 62, and 63. In some embodiments, rather than dedicating one sensor to each analyte (i.e., cocaine and BE and EME), a plurality of sensing elements can be dedicated to the detection of each of these analytes.

In other embodiments, a sensor according to the present teachings can be configured to detect amphetamines in a sample. Amphetamines are a group of synthetic psychoactive drugs called central nervous system (CNS) stimulants. The amphetamines include amphetamine, dextroamphetamine, and methamphetamine, where amphetamine is made up of two distinct compounds: pure dextroamphetamine and pure levoamphetamine.

In some embodiments, a sensor according to the present teachings can be configured to detect Ketamine (KT), which is a dissociative anesthetic used in human anesthesia and veterinary medicine. Dissociative drugs, such as KT, are hallucinogens that cause a person to feel detached from reality and hence can be abused.

More specifically, KT is a chiral anesthetic agent, (R)- and(S)-enantiomers of which differ in their pharmacological properties. KT has become one of the most commonly used illicit drugs in the world. Anti-KT antibodies are known. For example, an article entitled "Enantioselective Monoclonal Antibodies for Detecting Ketamine to Crack Down on Illicit Use," published in Bio Pharm Bull. 2018; 41 (1): 123-132, which is herein incorporated by reference in its entirety, describes the generation of monoclonal anti-KT antibodies. Briefly, this article describes that mice were immunized with either (a) commercially-available or (b) in-house-prepared KT-albumin conjugates. Splenocytes from these mouse groups (a and b) were separately fused with P3/NS1/1-Ag4-1 myeloma cells. After standard screening and cloning, 5 hybridoma clones were established from which antibodies were generated.

With reference to FIG. 1B, in such embodiments, the sensor can include a graphene layer that is functionalized with an antibody that exhibits a specific binding to an amphetamine. Anti-amphetamine antibodies suitable for use in the practice of various embodiments are commercially available. For example, MyBioSource, Inc. markets a mouse amphetamine monoclonal antibody under the catalog number MBS568115. In some such embodiments, a sensor according to the present teachings can exhibit a detection limit of 50 ng/ml for the detection of amphetamines in a sample.

In other embodiments, a sensor according to the present teachings can be configured to detect opiates. By way of example, in some such embodiments, a sensor according to the present teachings can be configured to detect morphine in a sample. With respect to FIG. 1B, in some such embodiments, the antibodies 16 can be selected to be anti-morphine antibodies. Such antibodies are commercially available. By way of example, a mouse anti-morphine antibody can be obtained from RayBiotech of Peachtree Corners, GA under catalogue number MD-18-0035. In some embodiments, a sensor according to the present teachings that is configured to detect morphine can exhibit a detection limit of 40 ng/ml (i.e., it can positively detect morphine in a sample when the concentration of the morphine in the sample is at least 40 ng/ml).

Figure 7:
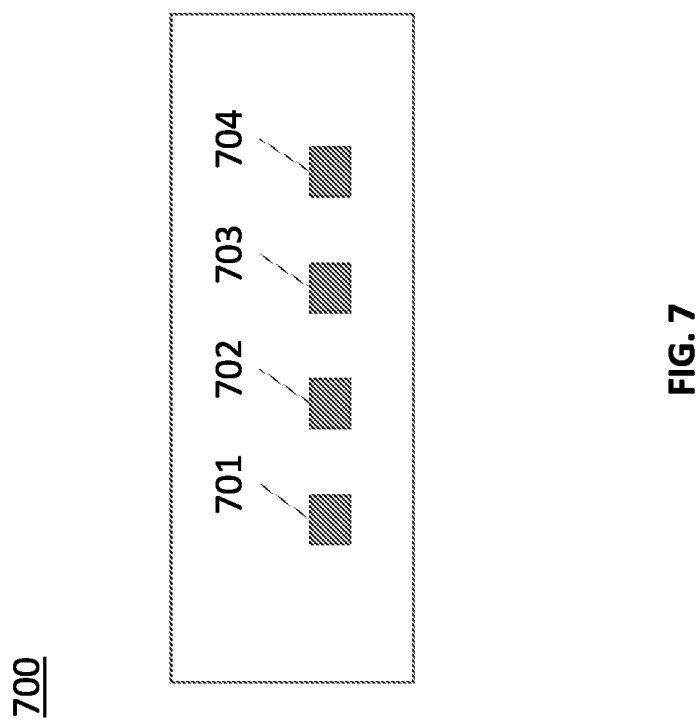

In some embodiments, a sensor according to the present teachings can include an array of graphene-based sensing elements that are configured for detecting different drugs of abuse. By way of example, FIG. 7 schematically depicts such a sensor 700 that includes four sensing elements 701, 702, 703, and 704, each of which is configured in a manner discussed above via functionalization of a graphene layer with an antibody. In this embodiment, the sensing element 701 can be configured to detect cocaine, the sensing element 702 can be configured to detect a cocaine metabolite, such as those discussed above, the sensing element 703 can configured to detect an amphetamine and the sensing element 704 can be configured to detect morphine. Other combination of sensing elements can be also be provided.

Figure 8:
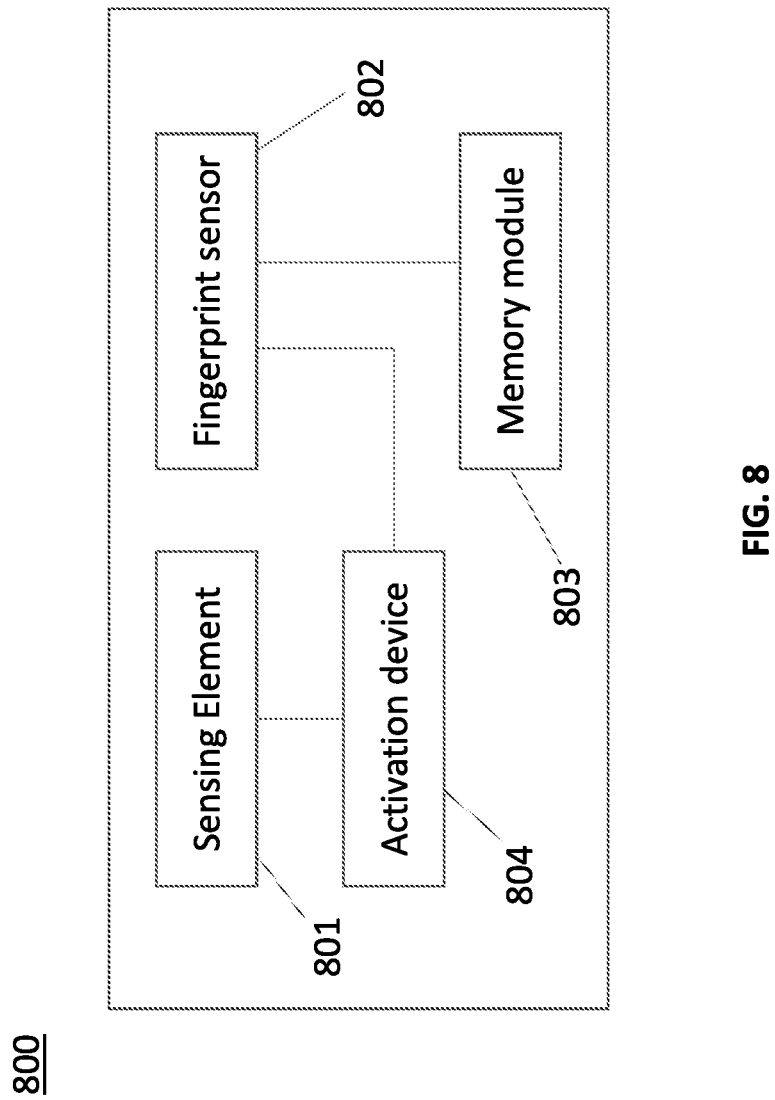

In some embodiments, a sensor according to the present teachings can be configured to include a biometric identification device. For example, in this embodiment, the biometric identification device is a fingerprint sensor. The sensor can further include an activation system that allows the use of the sensor only after the fingerprint sensor has indicated that a fingerprint has been detected and stored in memory. By way of example, FIG. 8 schematically depicts such a sensor 800 that includes a sensing element 801, such as the above sensing elements, and a fingerprint sensor 802, and at least one memory module 803 in communication with the fingerprint sensor 802 to store fingerprint data. The sensor 800 further includes an activation system 804 in communication with the fingerprint sensor 802 that can activate the sensor for receiving a sample only after the fingerprint sensor generates a signal indicating that a fingerprint has been read and stored in the memory module.

In some embodiments, the fingerprint data stored in the memory module 803 can be encrypted and/or encoded. In some embodiments, the fingerprint data can be stored after the user is verified by a separate means. By way of example, the user can be required to enter a password, personal identification number, or a one-time password (OTP).

In other embodiments, the sensor 800 can be activated upon verifying that the biometric information of the person who is attempting to use the sensor 800 is matched with pre-stored biometric information. The pre-stored biometric information can be stored within the memory module 803 of the sensor 800. In some embodiments, the pre-stored biometric information can be stored on a remote server, which is in wired/wireless communication with the sensor 800. The remote server can belong to or be under control of a law enforcement agency. For communication with the remote server, the sensor 800 can use the communication module 612.

Figure 9:
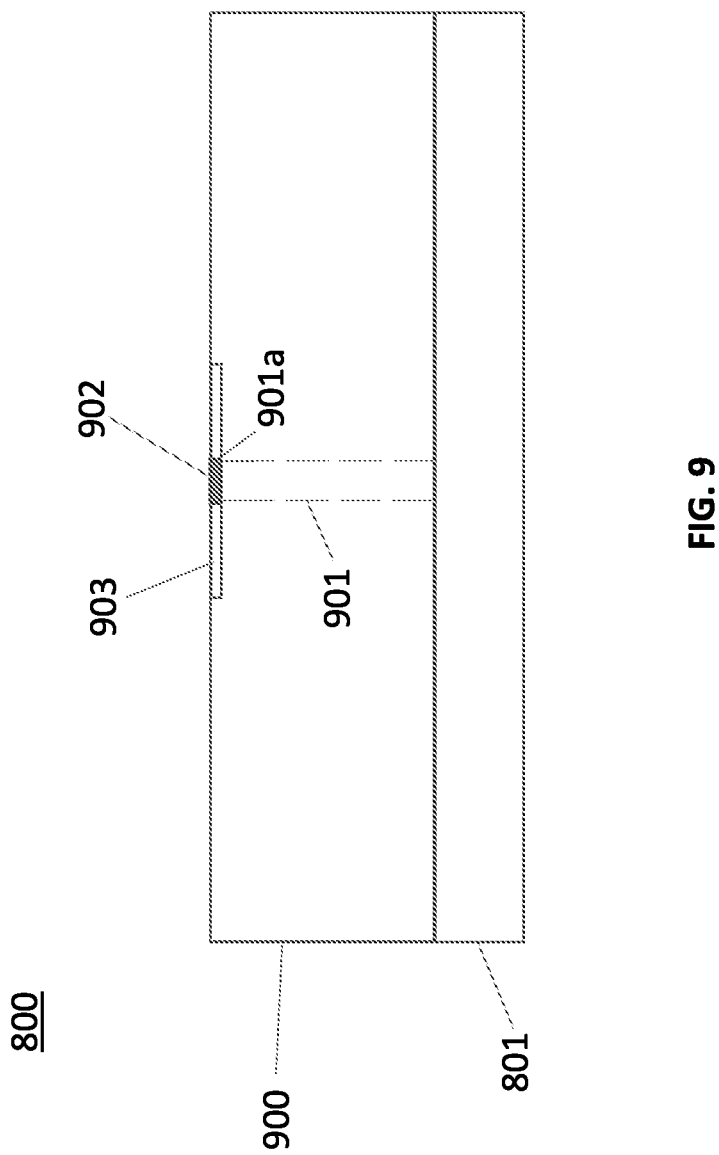
FIG. 9 is a schematic view of a microfluidic delivery system that can be incorporated into the sensor depicted in FIG. 8.

By of example, with reference to FIG. 9, similar to the sensor 100 as shown in FIG. 1A discussed above, the sensor 800 can include a microfluidic delivery system 900 that includes a microfluidic channel 901 for guiding a sample from an inlet port 901a of the microfluidic delivery system to the sensing element 801. A polymeric layer 902 covers the inlet port 901a to regulate access to the sensing element 801.

Figure 10:
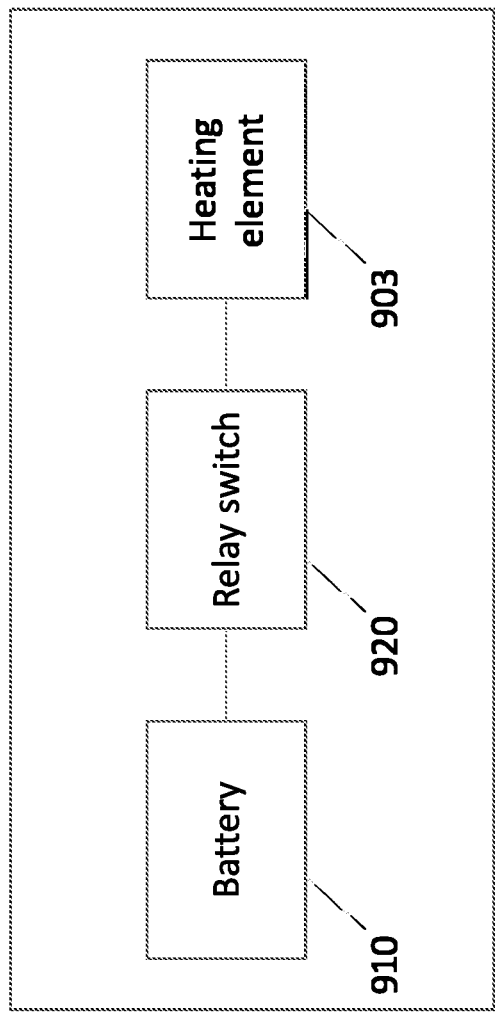
FIG. 10 is an example of an implementation of the activation device that can be employed in the sensor depicted in FIGS. 8 and 9.

With reference to FIG. 10, in this embodiment, the activation system 804 can include a heating element 903 that at least partially surrounds the polymeric layer 902 and is in thermal communication therewith. Further, the activation system 804 can include an energy source 910, such as a battery, that can provide energy to the heating element 903 and a relay switch 920 that can regulate the application of energy from the energy source 910 to the heating element.

The fingerprint sensor 802 can be in communication with the relay switch 920 and can provide a signal to the relay switch 920 to connect the heating element 903 to the energy source 910, thereby energizing the heating element. The heat generated by the heating element can cause melting of the thin polymeric layer, thereby providing access to the microfluidic channel 901 through which a sample can be delivered to the sensing element 801.

In other embodiments, the activation system 804 can be operably coupled to a circuitry, such as the above measurement circuitry 301, which is employed to measure an electrical property of the functionalized graphene layer, so as to activate the circuitry 301 only after the sensor has received biometric identification data. By way of example, the activation circuitry can activate a transistor switch to allow the circuitry to apply a voltage or a current to the functionalized graphene layer.

By way of example, in some embodiments, the fingerprint sensor 802 can be implemented based on the teachings of USRE45601E1 as informed by the present teachings. USRE45601E1 titled "Fingerprint sensing circuit having programmable sensing patterns," which is incorporated herein by reference in its entirety, describes a fingerprint sensor with programmable sensing patterns and multiple 1/0 interconnects. The 1/0 interconnects are configured to sequentially drive the plurality of fingerprint sensing elements. A memory device may be operably coupled to the fingerprint sensing circuit. A programmable data structure, such as a table, file, character string, numeric value, array, or the like may be stored in the memory device to designate a pattern for driving the fingerprint sensing elements. The fingerprint sensing circuit is configured to drive the fingerprint sensing elements according to the designated pattern.

In other embodiments, rather than a fingerprint sensor, other biometric sensors can be employed in the practice of various embodiments. Examples of such a biometric sensor can be an iris recognition sensor, a face recognition sensor, a voice recognition sensor, a vascular pattern recognition sensor, etc. Examples of biometric sensors to identify a user can be found in Allyn (U.S. Patent Application Publication No. US 2016/0283703), which is incorporated herein by reference in its entirety.

In use, when an individual is tested for a drug of abuse, the test administrator, e.g., a law enforcement official, can ask the individual to use the fingerprint sensor to record his/her fingerprint and subsequently provide an oral fluid sample, e.g., using known collection devices. The sample can then be introduced into the sensor for detection of one or more drugs of abuse. The entire process including the scanning of the fingerprint, providing an oral fluid sample, and the delivery of the oral fluid sample to the sensor, can be recorded to provide an appropriate chain of custody. As noted above, an analyzer, such as the analyzer discussed above, can then be employed to receive signals generated by the sensor and the signals can be analyzed in a manner disclosed herein to determine whether an analyte of interest (e.g., cocaine, a cocaine metabolite, amphetamine, or opiate) is present in a sample at a concentration above the sensor's limit of detection. In some embodiments, the data can be transmitted to a remote location, e.g., to a law enforcement agency.

Those having ordinary skill in the art will appreciate that various changes can be made to the above embodiments without departing from the scope of the present invention.

CONCLUSION AND GENERAL TERMINOLOGY

In various embodiments, one or more of disclosed modules are implemented via one or more computer programs for performing the functionality of the corresponding modules, or via computer processors executing those programs. In some embodiments, one or more of the disclosed modules are implemented via one or more hardware modules executing firmware for performing the functionality of the corresponding modules. In various embodiments, one or more of the disclosed modules include storage media for storing data used by the module, or software or firmware programs executed by the module. In various embodiments, one or more of the disclosed modules or disclosed storage media are internal or external to the disclosed systems. In some embodiments, one or more of the disclosed modules or storage media are implemented via a computing "cloud", to which the disclosed system connects via a network connection and accordingly uses the external module or storage medium. In some embodiments, the disclosed storage media for storing information include non-transitory computer-readable media, such as a CD-ROM, a computer storage, e.g., a hard disk, or a flash memory. Further, in various embodiments, one or more of the storage media are non-transitory computer-readable media that store data or computer programs executed by various modules, or implement various techniques or flow charts disclosed herein.

The above detailed description refers to the accompanying drawings. The same or similar reference numbers may have been used in the drawings or in the description to refer to the same or similar parts. Also, similarly named elements may perform similar functions and may be similarly designed, unless specified otherwise. Details are set forth to provide an understanding of the exemplary embodiments. Embodiments, e.g., alternative embodiments, may be practiced without some of these details. In other instances, well known techniques, procedures, and components have not been described in detail to avoid obscuring the described embodiments.

The foregoing description of the embodiments has been presented for purposes of illustration only. It is not exhaustive and does not limit the embodiments to the precise form disclosed. While several exemplary embodiments and features are described, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a," "the," "one," "one or more," "some," or "various" embodiments. As used herein, the singular forms "a," "an," and "the" may include the plural forms unless the context clearly dictates otherwise. Further, the term "coupled" does not exclude the presence of intermediate elements between the coupled items. Also, stating that a feature may exist indicates that the feature may exist in one or more embodiments.

In this disclosure, the terms "include," "comprise," "contain," and "have," when used after a set or a system, mean an open inclusion and do not exclude addition of other, non-enumerated, members to the set or to the system. Further, unless stated otherwise or deducted otherwise from the context, the conjunction "or," if used, is not exclusive, but is instead inclusive to mean and/or. Moreover, if these terms are used, a subset of a set may include one or more than one, including all, members of the set.

The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the systems described need not necessarily include all parts described in the embodiments, and may also include other parts not described in the embodiments. Accordingly, the embodiments are not limited to the above-described details, but instead are defined by the appended claims in light of their full scope of equivalents. Further, the present disclosure is directed toward all novel and non-obvious features and aspects of the various disclosed embodiments, alone and in various combinations and sub-combinations with one another.

While the present disclosure has been particularly described in conjunction with specific embodiments, many alternatives, modifications, and variations will be apparent in light of the foregoing description. It is therefore contemplated that the appended claims will embrace any such alternatives, modifications, and variations as falling within the true spirit and scope of the present disclosure.

What is claimed is:

1. A sensor for detecting a drug of abuse (DOA) in a sample, comprising:
   a plurality of sensing elements, each of said plurality of sensing elements comprising:
   a graphene layer;
   a plurality of binding agents that specifically bind to said DOA coupled to said graphene layer to generate a functionalized graphene layer; and
   a plurality of electrical conductors electrically coupled to said functionalized graphene layer for measuring an electrical property of said functionalized graphene layer, and providing a signal indicative of a presence of the DOA,
   wherein the signals provided by the plurality of sensing elements are averaged to provide a resultant signal indicative of a presence of the DOA and, wherein at least one of the sensing elements can be configured as a calibration sensing element to quantify an amount of the DOA that is present in the sample.

2. A disposable cartridge for detecting a drug of abuse (DOA) in a sample, comprising:
   a microfluidic component having an inlet port for receiving a sample and an exit port; and
   a sensor fluidically coupled to said microfluidic component to receive at least a portion of said sample from said exit port,
   wherein said sensor comprises:
   a plurality of sensing elements, each of said plurality of sensing elements comprising:
   a graphene layer;
   a plurality of binding agents that bind to said DOA coupled to said graphene layer to generate a functionalized graphene layer; and
   a plurality of electrical conductors electrically coupled to said functionalized graphene layer for measuring an electrical property of said functionalized graphene layer, and providing a signal indicative of a presence of the DOA,
   wherein the signals provided by the plurality of sensing elements are averaged to provide a resultant signal indicative of a presence of the DOA and, wherein at least one of the sensing elements can be configured as a calibration sensing element to quantify an amount of the DOA that is present in the sample.

* * * * *